(12) United States Patent
Chomczynski

(10) Patent No.: US 6,723,755 B2
(45) Date of Patent: Apr. 20, 2004

(54) METHOD OF TREATING ROSACEA

(76) Inventor: Piotr Chomczynski, 14 Elmhurst Pl., Cincinnati, OH (US) 45208

( * ) Notice: Subject to any disclaimer, the term of this patent is extended or adjusted under 35 U.S.C. 154(b) by 0 days.

(21) Appl. No.: 10/430,917

(22) Filed: May 7, 2003

(65) Prior Publication Data

US 2003/0232893 A1 Dec. 18, 2003

Related U.S. Application Data

(60) Provisional application No. 60/388,373, filed on Jun. 12, 2002.

(51) Int. Cl.$^7$ ............................................. A61K 31/045
(52) U.S. Cl. ..................................................... 514/729
(58) Field of Search ......................................... 514/729

(56) References Cited

U.S. PATENT DOCUMENTS

| | | |
|---|---|---|
| 5,641,809 A | 6/1997 | Hagen et al. |
| 5,654,312 A | 8/1997 | Andrulis, Jr. et al. |
| 5,885,595 A | 3/1999 | Corey et al. |
| 5,886,233 A | 3/1999 | Steinmeyer et al. |
| 5,895,649 A | 4/1999 | de Lacharriere et al. |
| 5,932,215 A | 8/1999 | de Lacharriere et al. |
| 5,952,372 A | 9/1999 | McDaniel |
| 5,968,532 A | 10/1999 | de Lacharriere et al. |
| 5,969,190 A * | 10/1999 | Bauer et al. ................. 568/400 |
| 5,972,892 A | 10/1999 | de Lacharriere et al. |
| 5,972,993 A | 10/1999 | Ptchelintsev |
| 5,994,330 A | 11/1999 | El Khoury |
| 5,998,395 A | 12/1999 | Kligman |
| 6,028,118 A | 2/2000 | Dupont et al. |
| 6,054,475 A | 4/2000 | Martin et al. |
| 6,057,341 A | 5/2000 | Charpentier |
| 6,057,453 A | 5/2000 | Yang et al. |
| 6,071,541 A | 6/2000 | Murad |
| 6,071,955 A | 6/2000 | Elias et al. |
| 6,184,422 B1 | 2/2001 | Barbier et al. |
| 6,277,837 B1 | 8/2001 | DeLuca, Jr. et al. |
| 6,462,075 B1 * | 10/2002 | Bowen et al. ............... 514/460 |
| 2002/0049257 A1 * | 4/2002 | Natsch ......................... 514/715 |

FOREIGN PATENT DOCUMENTS

WO     WO 98 11882 A    3/1998

OTHER PUBLICATIONS

US 6,290,937, 9/2001, Brown et al. (withdrawn)*
Browning and Proia, "Ocular Rosacea," Survey of Ophthalmology, vol. 31, No. 3, Nov.–Dec. 1986, pp. 145–158.
Müller–Decker et al., "The release of inflammatory mediators from human keratinocytes in cell cultures as an indication of skin irritation: Development of a replacement for animal studies," Aktuelle Dermatologies. vol. 23, No. 3 (1997) pp. 72–77.
Budavari, Ed., AA*Merck Index*, 12$^{th}$ ed., "6242. Metronidazole," Merck & Co., New Jersey, 1996, p. 1051.

* cited by examiner

*Primary Examiner*—James H Reamer
(74) *Attorney, Agent, or Firm*—Frost Brown Todd LLC

(57) ABSTRACT

A method for topically treating rosacea is disclosed. In this method, an active material having the formula given below is applied to the patient at the site of said rosacea:

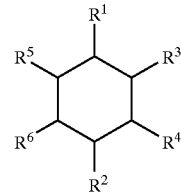

wherein $R^1$ is selected from —OH and $C_1$–$C_3$ alkyl OH; and $R^2$, $R^3$, $R^4$, $R^5$ and $R^6$ are independently selected from —H, —OH, $C_1$–$C_6$ alkyl, and $C_3$–$C_6$ cycloalkyl. Preferred active materials include 1,2-cyclohexanediol, 1,3-cyclohexanediol, 1,4-cyclohexanediol, and mixtures of those materials. Methods for treating acne vulgaris, as well as colds, flu, sinusitis, and ear infections, using these actives are also disclosed.

13 Claims, No Drawings

METHOD OF TREATING ROSACEA

CROSS-REFERENCE TO RELATED APPLICATION

This application is based upon and claims priority from U.S. Provisional Application No. 60/388,373, filed Jun. 12, 2002, incorporated herein by reference.

TECHNICAL FIELD

The present invention relates to methods for the topical treatment of rosacea.

BACKGROUND OF THE INVENTION

Rosacea is a common chronic skin condition characterized by a spectrum of clinical indications including flushing episodes, erythema, telangiectasia, inflammatory papulopustular eruptions resembling acne, and ocular symptoms. Although accurate incidence data for the U.S. are not available, data obtained in Sweden suggest that some form of rosacea may be present in up to 10% of the average population. Sufferers are mostly of European origin, generally with fair skin and blue eyes. Women are more prone to develop rosacea than men, with flushing episodes and erythema being the most common symptoms found.

The etiology of rosacea is unknown, but it is presumed to be a genetically determined anomalous vascular response that develops in the third to sixth decades of life. The hypothesis that the basic pathogenesis of the disease is a flushing disorder is based on several findings. The disease appears to more prevalent in northern climates where cold exposure is experienced more often, and in light-skinned persons in whom flushing is common and sensitivity to sunlight is particularly high. Accordingly, rosacea may represent a type of hypersensitivity reaction disease in which vascular sensitivity is a central mechanism in its etiology. The correlation between sensitive blood vessels and sensitive skin has, however, not yet been determined. Epidemiological studies suggest that the regulatory mechanism of blood vessels may be of importance in the onset and development of rosacea. Studies show that 27% of rosacea patients were found to suffer from migraine and 42% from a tendency to flush, both of which represent about twice the level that would typically be found in a control group.

An etiological role has also been proposed for the Demodex species, mites that normally inhabit human hair follicles and are reported to appear in greater numbers in rosacea patients. A number of dietary factors, for example hot drinks, alcohol, spicy foods, and environmental conditions (e.g., temperature changes), are well-recognized triggers of the disease. In literature, there are also reports of possible involvement of altered immune function and anomalously low skin surface lipids in the pathogenesis of rosacea.

The key to successful management of rosacea is early diagnosis and treatment. Treatment is generally aimed at controlling the symptoms and making the skin look better. At the present time, rosacea cannot be cured, though the frequency of its flare-ups can be diminished and their severity alleviated. Most cases of rosacea can be controlled with anti-inflammatory medications, combined with the avoidance of lifestyle and environmental factors that may aggravate the disorder in individual cases. Treatment generally works best at improving the pimples and bumps of rosacea; the redness of the skin is harder to treat. Therapeutic agents for inflammatory rosacea conditions are generally classified in two groups: (1) systemic and topical antibiotics; and (2) retinoids. Systemic and topical antibiotics include tetracycline, metronidazole, erythromycin, minocycline and clindamycin, but the use of these agents is often accompanied by drug side effects, the development of resistance, and changes in the normal microbial flora. Retinoids include tretinoin (vitamin A or retinoic acid), which is applied topically to inhibit follicular keratinization, and isotretinoin (13-cis-retinoic acid), which is administered systemically to suppress activity of the sebaceous glands. Retinoids are often irritants and are not advised for individuals with sensitive skin. Retinoids can also be phototoxic and they can induce thin and easily bruisable, fragile skin.

Metronidazole (5-methyl-5-nitroimidazole-1-ethanol), an antibacterial, is currently one of the more frequently prescribed treatments for rosacea in the United States. It is available as a topical cream under the name Metrogel™ from Galderma. Metronidazole is structurally similar to some materials which are believed to be carcinogens and is, in fact, listed by the U.S. Environmental Protection Agency as reasonably anticipated to be a human carcinogen. See *Merck Index,* 1996, page 1051.

Thus, there is a need for a safe and effective topical treatment of the symptoms of rosacea which not only act quickly and effectively, but which present reduced side effects when compared to the current treatment modalities.

Methods for treating rosacea have been described in the patent literature. Recent examples include the following patents.

U.S. Pat. No. 5,932,215, De Lacharriere, et al., issued Aug. 3, 1999, describes a method for the topical and systemic treatment of rosacea using an antagonist of CGRP (calcitonin gene-related peptide).

U.S. Pat. No. 5,972,993, Ptchelintsev, issued Oct. 26, 1999, describes a method for treating rosacea and sensitive skin conditions using certain specifically-defined antioxidant materials.

U.S. Pat. No. 5,952,372, McDaniel, issued Sep. 14, 1999, describes a method for treating rosacea using oral or topically applied ivermectin. This method of treatment is aimed at reducing or eliminating the Demodex organisms which are frequently found on the skin of rosacea patients.

U.S. Pat. No. 5,654,312, Andrulis, Jr., et al., issued Aug. 5, 1997, describes a method for the systemic or topical treatment of inflammatory or autoimmune dermatoses using thalidomide, either alone or in combination with a cytokine inhibitor or a growth factor inhibitor.

U.S. Pat. No. 5,998,395, Kligman, issued Dec. 7, 1999, describes a method for suppressing inflammation in an inflammatory dermatosis, such as rosacea, using a topically applied composition containing both a corticosteroid and a retinoid.

U.S. Pat. No. 6,028,118, Dupont et al., Feb. 22, 2000, describes the use of a shark cartilage extract as an anti-angiogenic, anti-inflammatory and anti-collagenolytic material which may be used in the treatment of rosacea.

U.S. Pat. No. 5,994,330, El Khoury, issued Nov. 30, 1999, describes the treatment of acne and other inflammatory skin conditions using topically administered muscarinic agents. The therapeutic effects of the invention are said to include a decrease in redness, swelling and inflammation.

U.S. Pat. No. 5,968,532, De Lacharriere, et al., issued Oct. 19, 1999, describes the use of an ethylene diamine derivative in a cosmetic or dermatological composition containing a material having an irritant side effect. The ethylene diamine derivative is said to minimize skin irritation, erythema and sensations of inflammation or rosacea stemming from the use of the cosmetic/dermatological product.

U.S. Pat. No. 6,071,955, Elias, et al., issued Jun. 6, 2000, describes the use of juvenile hormone III to treat acne or acneiform conditions. The compounds is said to act as an activator of the receptors XFR, PPARA and LXRA.

U.S. Pat. No. 5,885,595, Corey, et al., issued Mar. 23, 1999, describes a cosmetic composition which includes a retinol fatty acid ester. The composition is said to be effective for treating chronoaging conditions of the skin and dermatological disorders including acne, follicular and lesional papules, actinic keratoses, oily skin and rosacea.

U.S. Pat. No. 5,895,649, De Lacharriere, et al., issued Apr. 20, 1999, describes a method for treating neurogenic red skin blotches, including those present with rosacea, using the topical application of a TNF-alpha antagonist.

U.S. Pat. No. 6,071,541, Murad, issued Jun. 6, 2000, describes the use of a topical composition which contains a hydroxy acid or tannic acid to exfoliate a portion of the skin, stabilized hydrogen peroxide to facilitate cleansing of the skin, and an antimicrobial agent to inhibit or reduce microorganisms on the skin. The composition is said to be effective in the treatment and management of inflammatory skin conditions, such as acne and acneiform rosacea.

U.S. Pat. No. 5,972,892, De Lacharriere, et al., issued Oct. 26, 1999, describes a therapeutic composition for topical application containing at least one material having an irritant side effect together with a substance P antagonist for reducing or eliminating the irritant effect of this material. The substance P antagonist may be a peptide compound or a nitrogen-containing compound or a nitrogen-, sulfur- or oxygen-containing heterocyclic compound.

U.S. Pat. No. 6,057,341, Charpentier, issued May 2, 2000, describes pharmaceutical or cosmetic compositions which include novel bi-aromatic dibenzofuran derivatives. The compositions are said to exhibit pharmacological responses of the retinoid agonist type and are further said to be effective in treating keratinization disorders, including acne rosacea.

U.S. Pat. No. 6,054,475, Martin, et al., issued Apr. 25, 2000, describes the use of substituted dihydrobenzofuran-based phosphodiesterase-4 inhibitors for the treatment of proliferative, inflammatory and allergic dermatoses, including acne rosacea.

U.S. Pat. No. 6,057,453, Yang, et al., issued May 2, 2000, and U.S. Pat. No. 6,060,604, Yang, et al., issued May 9, 2000, describe a novel class of polyamines substituted with electron-affinic groups. These materials are said to be effective in the treatment of dermatological conditions caused by anaerobic and microaerophilic microorganisms.

Organic alcohols, diols and polyols have been disclosed for use in the treatment of a variety of dermatological conditions.

U.S. Pat. No. 6,290,937, Brown, et al., issued Sep. 18, 2001, and which has been withdrawn from issue by the Patent Office, described a series of pharmaceutical compositions which were said to increase the melanin content of mammalian melanocytes and which were also said to be useful for treating skin proliferative disorders, such as acne vulgaris. The compositions disclosed may utilize $C_3$–$C_{50}$ diols as the pharmaceutically active agent; 1,2-cis- and 1,2-trans-cyclohexanediol are specifically disclosed as active ingredients. In addition, 1,2-cis-cyclopentanediol was among the preferred active compounds. The treatment of rosacea was not disclosed or suggested. Since this patent has been withdrawn from issue, it does not constitute prior art.

U.S. Pat. No. 6,184,422, Barbier, et al., issued Feb. 6, 2001, discloses a group of unsaturated long-chain (for example, $C_{12}$) derivatives of cyclohexanediol. These materials are taught to be useful topically for the treatment of hyperproliferative diseases and diseases of the sebaceous glands, such as acne. See also related U.S. Pat. No. 5,969, 190.

U.S. Pat. No. 5,886,233, Steinmeyer, et al., issued Mar. 23, 1999, describes cyclohexanone derivatives used to synthesize vitamin D compounds. The compounds are said to be useful for treating skin, such as in the treatment of acne.

U.S. Pat. No. 6,277,837, DeLuca, Jr., et al., issued Aug. 21, 2001, describes a group of vitamin D-related compounds which include a cyclohexanediol moiety. The compositions are taught to be useful for the treatment of cell proliferation diseases, such as psoriasis. See also related U.S. Pat. Nos. 6,127,559; 5,945,410; 5,936,133; and 5,843,928.

U.S. Pat. No. 5,641,809, Hagen, et al., issued Jun. 24, 1997, describes a skin treatment composition that includes lanolin together with an ester of a lanolin acid. The patent teaches that lanolin includes $C_9$–$C_{22}$ diols as one of its components. The treatment of rosacea is not disclosed or suggested.

SUMMARY OF THE INVENTION

The present invention relates to a method of treating rosacea in humans comprising topically applying to a patient in need of such treatment a safe and effective amount (for example, from about 0.05 to about 1 mg/cm$^2$) of the compound having the following formula, at the site of said rosacea or where said patient is prone to exhibit rosacea:

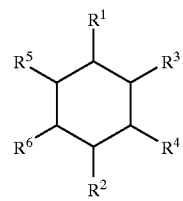

wherein $R^1$ is selected from —OH and $C_1$–$C_3$ alkyl OH (alkanols), and $R^2$, $R^3$, $R^4$, $R^5$ and $R^6$ are each independently selected from —H, —OH, $C_1$–$C_6$ alkyl and $C_3$–$C_6$ cycloalkyl.

Particularly preferred compounds are cyclohexanol, 1,2-cyclohexanediol, 1,3-cyclohexanediol, and 1,4-cyclohexanediol, and mixtures of those materials. The active material may be administered with a pharmaceutical carrier.

The present invention also encompasses a method for treating acne vulgaris in humans comprising topically applying to the affected site of a patient in need of such treatment a safe and effective amount of an active compound defined herein, such as 1,3-cyclohexanediol, 1,4-cyclohexanediol, and mixtures thereof.

Finally, the present invention encompasses the treatment of conditions characterized by inflammatory or allergy symptoms, such as colds, flu, sinusitis, and ear infections, by the topical application of an effective amount of the active materials defined herein.

All percentages and ratios given herein are by weight, unless otherwise specified.

All patents and other publications cited in this application are incorporated herein by reference.

DETAILED DESCRIPTION OF THE INVENTION

As used herein, the term "safe and effective amount" is intended to define that amount of active material or a pharmaceutical composition containing said active material which is used to provide effective treatment for the condition being treated, such as rosacea, acne vulgaris or conditions characterized by inflammation and allergy symptoms (such as colds, flu, sinusitis, or ear infections), without providing the user with a significant risk of side effects that accompany the use of any pharmaceutically-active material.

The present invention provides a method of treating rosacea utilizing the topical application of a pharmaceutically-active material. The pharmaceutically-active material has the following formula:

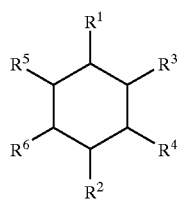

In this formula, $R^1$ is selected from OH and $C_1$–$C_3$ alkyl OH($C_1$–$C_3$ alkanols); and $R^2$, $R^3$, $R^4$, $R^5$ and $R^6$ are independently selected from —H, —OH, $C_1$–$C_6$ alkyl and $C_3$–$C_6$ cycloalkyl. In this formula it is preferred that $R^2$, $R^3$, $R^4$, $R^1$ and $R^6$ be selected from —H and —OH, and further that the molecule in its entirety contain no more than two hydroxyl groups. Preferred compounds for use in the present invention are selected from cyclohexanol, 2-cyclohexylethanol, cyclohexylmethanol, 3-cyclohexyl-1-propanol, 1,4-cyclohexanediol (both the cis and trans isomers), 1,3-cyclohexanediol (both the cis and trans isomers), 1,2-cyclohexanediol (both the cis and trans isomers), 4,-cyclohexylcyclohexanol, and 4-methylcyclohexanol (both the cis and trans isomers). Mixtures of these materials may also be used. Stereochemical isomers are intended to be included within these compound definitions.

Related materials which have been tested and found not to be useful in the present invention include cyclohexane, cyclohexene, cyclohexyl acetate, cyclohexyl chloride, 4-cyclohexyl-1-butanol, cyclohexyl carboxylic acid, 1-methylcyclohexanol, and menthol. In fact, menthol not only does not provide a benefit for use in the treatment of rosacea, but it also can irritate (and thereby redden) the skin to which it is applied. Other materials which do not work in the present invention include 1,2-cyclopentanediol (both the cis and trans isomers), 5-norborene-2,2-dimethanol, and (1R,2R,3S,5S-(−))-pinanediol.

Particularly preferred compounds for use in the present invention include 1,2-cyclohexanediol (the cis and trans isomers thereof), 1,3-cyclohexanediol (the cis and trans isomers thereof), 1,4-cyclohexanediol (the cis and trans isomers thereof), and mixtures of those materials. The various optical isomers of these materials are active in the present invention as well.

The active material is applied topically to the skin at the site of rosacea, or at the site where the patient is prone to exhibit rosacea if the invention is used in a prophylactic/preventive mode. The active material is typically applied to the skin in an amount of from about 0.05 to about 1 mg/cm$^2$, preferably from about 0.3 to about 0.5 mg/cm$^2$, but this can vary depending upon the formulation, the patient and the nature of the specific condition being treated.

The active material may be applied in combination with a topical carrier. Topical carriers are well known in the art and are described, for example, in U.S. Pat. No. 6,376,514, Degenhardt, et al., issued Apr. 23, 2002; U.S. Pat. No. 6,380,168, Kubo, et al., issued Apr. 30, 2002; and U.S. Pat. No. 6,368,831, Maurer, et al., issued Apr. 9, 2002; all of which are incorporated herein by reference. When used with a topical carrier, the active material and the topical carrier together comprise a topical composition. In such topical compositions, the active material generally comprises from about 1% to about 50% of the composition, preferably from about 1% to about 20% of the composition, most preferably from about 2% to about 10% of the composition, with the balance of the composition generally comprising the topical carrier. The topical carrier is a material or mixture of materials which is compatible with the active material, is non-irritating when applied to the skin and, may, provide cosmetic benefits or aid penetration of the active material into the skin.

The carrier may comprise a single ingredient or a combination of two or more ingredients. Preferred topical carriers comprise one or more ingredients selected from the group including water, alcohols, aloe vera gel, allantoin, glycerin, vitamin A and E oils, mineral oil, propylene glycol, polypropylene glycol-2 myristyl propionate, dimethylisosorbide, and combinations thereof. Particularly preferred carriers include propylene glycol, dimethylisosorbide, water, and mixtures of those materials.

The topical carrier may comprise one or more ingredients selected from the group consisting of emollients, propellants, solvents, humectants, thickeners, powders and fragrances, in addition to, or instead of, the preferred topical carrier ingredients listed above. One skilled in the art would be able to select and optimize carrier ingredients for the topical compositions used in the present invention without undue experimentation.

If an emollient is included in the carrier, it is typically included at a level of from about 5% to about 95% of the total carrier. Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, myristyl myristate, polydimethylsiloxane, and mixtures of those material. Preferred emollients include stearyl alcohol and polydimethylsiloxane.

If a propellant is used, it is typically used at from about 5% to about 95% of the topical carrier. Suitable propellants include propane, butane, isobutane, dimethyl ether, carbon dioxide, nitrous oxide, nitrogen, and mixtures of those materials.

If a solvent is used, it is typically used at from about 5% to about 95% of the topical carrier. Suitable solvents include, for example, water, ethanol, methylene chloride, isopropanol, castor oil, ethylene glycol monoethyl ether, diethylene glycol monobutyl ether, diethylene glycol monoethyl ether, dimethyl sulfoxide, dimethyl formamide, tetrahydrofuran, glycols, including propylene glycol, and mixtures of those materials. Preferred solvents include ethyl alcohol, water, glycols, and mixtures of those materials.

If a humectant is used in the topical carrier, it is typically used at from about 5% to about 95%. Suitable humectants include, for example, glycerin, sorbitol, sodium 2-pyrrolidone-5-carboxylate, soluble collagen, dibutyl phthalate, gelatin, and mixtures of those materials. A preferred humectant is glycerin.

If a thickener is used in the topical carrier, it is typically used at from about 0.1% to about 95% of the carrier composition. The carrier composition may also include powders for the purpose of providing various desirable rheological properties to the final composition. Typically, such powder materials are used at relatively low levels, generally from about 0% to about 25% of the topical carrier. Exemplary powders include chalk, talc, fullers earth, kaolin, starch, gums, colloidal silicon dioxide, sodium polyacrylate, tetraalkylammonium smectites, trialkylaryl smectites, chemically modified magnesium aluminum silicate, organically-modified montmorillonite clay, hydrated aluminum silicate, fumed silica, carboxyvinyl polymer, sodium carboxymethyl cellulose, ethylene glycol monostearate, and mixtures of those materials. If a fragrance is included in the topical carrier, it is typically used at from about 0.001% to about 0.5% of the carrier.

Waxes may also be included in the topical carrier, primarily for their ability to provide desirable Theological properties, such as viscosity, to the carrier. Examples of suitable waxes include animal waxes, vegetable waxes, mineral waxes, various fractions of natural waxes, synthetic waxes, petroleum waxes, ethylenic polymers, hydrocarbon types such as Fischer-Tropsch waxes, silicone waxes and mixtures of such materials having a melting point between about 40° C. and 100° C.

Techniques for formulating topical carriers and topical pharmaceutical compositions which may be used in the present invention are described in the following references: *Modern Pharmaceutics*, Chapters 9 and 10, Banker & Rhodes, eds. (1979); Lieberman et al., *Pharmaceutical Dosage Forms* (1981); and Ansel, *Introduction to Pharmaceutical Dosage Forms*, $2^{nd}$ edition, (1976), all incorporated herein by reference. Topical compositions that can be applied locally to the skin may be in any form including solutions, oils, creams, ointments, gels, lotions, sprays, skin patches, and the like.

The present invention also relates to a method for treating acne vulgaris in humans comprising the topical application (at the site requiring treatment) to a patient in need of such treatment of a safe and effective amount of a compound selected from cyclohexanol and cyclohexanol derivatives, such as 1,3-cyclohexanediol, 1,4-cyclohexanediol, and mixtures thereof. Generally, the active material is applied in an amount of from about 0.05 to about 1 mg/cm², preferably from about 0.3 to about 0.5 mg/cm². The active materials may be used in combination with a topical carrier such as those described above. Stereoisomers and optical isomers of the active materials may be used.

Finally, it has been found that topical application of the active materials defined herein can be used to treat conditions characterized by inflammation and allergy symptoms, such as colds, flu, sinusitis, and ear infections. The active material is applied at a site proximate to the nose, mouth and/or ears of the patient. Preferred active materials include cyclohexanol, 2-cyclohexylethanol, cyclohexylmethanol, 3-cyclohexyl-1-propanol, 1,4-cyclohexanediol (both the cis and trans isomers), 1,3-cyclohexanediol (both the cis and trans isomers), 1,2-cyclohexanediol (both the cis and trans isomers), 4-cyclohexylcyclohexanol, and 4-methylcyclohexanol (both the cis and trans isomers), and mixtures thereof. Preferred materials include cyclohexanol, 1,3-cyclohexanediol, 1,4-cyclohexanediol, and mixtures thereof. Generally, the active material is applied in an amount of from about 0.05 to about 1 mg/cm², preferably from about 0.3 to about 0.5 mg/cm².

What is claimed is:

1. A method of treating rosacea in humans comprising topically applying to a patient in need of such treatment a safe and effective amount of the active compound having the following formula, at the site of said rosacea or where said patient is prone to exhibit rosacea:

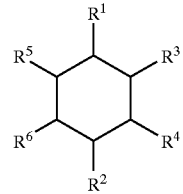

wherein $R^1$ is selected from —OH, and $C_1$–$C_3$ alkyl OH; and $R^2$, $R^3$, $R^4$, $R^5$ and $R^6$ are each independently selected from —H, —OH, $C_1$–$C_6$ alkyl and $C_3$–$C_6$ cycloalkyl.

2. The method according to claim 1 wherein the active compound is applied to the skin in an amount of from about 0.05 to about 1 mg/cm².

3. The method according to claim 2 wherein the active compound is applied to the skin in a pharmaceutically-acceptable carrier.

4. The method according to claim 3 wherein the active compound is selected from cyclohexanol, 2-cyclohexylethanol, cyclohexylmethanol, 3-cyclohexyl-1-propanol, 1,4-cyclohexanediol (cis and/or trans isomers), 1,3 cyclohexanediol (cis and/or trans isomers), 1,2-cyclohexanediol, 4-cyclohexylcyclohexanol, 4-methylcyclohexanol, and mixtures thereof.

5. The method according to claim 3 wherein the active compound contains no more than 2 hydroxyl groups.

6. The method according to claim 5 wherein the active compound is selected from 1,2-cyclohexanediol, 1,3-cyclohexanediol, 1,4-cyclohexanediol, and mixtures thereof.

7. The method according to claim 3 wherein $R^2$, $R^3$, $R^4$, $R^5$ and $R^6$ are independently selected from —H and —OH.

8. The method according to claim 3 wherein the pharmaceutical carrier is selected from propylene glycol, water, dimethylisosorbide, and mixtures thereof.

9. The method according to claim 6 wherein the pharmaceutical carrier is selected from propylene glycol, water, dimethylisosorbide, and mixtures thereof.

10. A method of treating acne vulgaris in humans comprising topically applying to a patient in need of such treatment a safe and effective amount of a compound selected from 1,3-cyclohexanediol, 1,4-cyclohexanediol, and mixtures thereof.

11. A method for treating conditions characterized by inflammation and allergy symptoms comprising topically applying to a patient in need of such treatment a safe and effective amount of a compound selected from cyclohexanol, 2-cyclohexylethanol, cyclohexylmethanol, 3-cyclohexyl-1-propanol, 1,4-cyclohexanediol (the cis and/or trans isomers), 1,3-cyclohexanediol (the cis and/or trans isomers), 1,2-cyclohexanediol (the cis and/or trans isomers), 4-cyclohexylcyclohexanol, and 4-methylcyclohexanol (the cis and/or trans isomers), and mixtures thereof.

12. The method according to claim 11 wherein the condition is selected from colds, flu, sinusitis, and ear infections.

13. The method according to claim 12 wherein the compound is selected from cyclohexanol, 1,3-cyclohexanediol, 1,4-cyclohexanediol, and mixtures thereof.

* * * * *

UNITED STATES PATENT AND TRADEMARK OFFICE
CERTIFICATE OF CORRECTION

PATENT NO. : 6,723,755 B2
DATED : April 20, 2004
INVENTOR(S) : Piotr Chomczynski It is certified that error appears in the above-identified patent and that said Letters Patent is hereby corrected as shown below:

Column 8,
Line 48, after, "selected from" and before "1,3-cyclohexanediol…" please insert -- 1,2-cyclohexanediol --.
Line 64, after, "…selected from cyclohexanol" and before "1,3-cyclohexanediol" please insert -- 1,2-cyclohexanediol --.

Signed and Sealed this

Seventh Day of December, 2004

JON W. DUDAS
*Director of the United States Patent and Trademark Office*